(12) United States Patent
Kraus

(10) Patent No.: US 9,617,236 B2
(45) Date of Patent: Apr. 11, 2017

(54) SYNTHESIS OF COUMALIC ACID

(71) Applicant: Iowa State University Research Foundation, Inc., Ames, IA (US)

(72) Inventor: George A. Kraus, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 14/892,298

(22) PCT Filed: May 20, 2014

(86) PCT No.: PCT/US2014/038784
§ 371 (c)(1),
(2) Date: Nov. 19, 2015

(87) PCT Pub. No.: WO2014/189926
PCT Pub. Date: Nov. 27, 2014

(65) Prior Publication Data
US 2016/0122311 A1    May 5, 2016

Related U.S. Application Data

(60) Provisional application No. 61/826,368, filed on May 22, 2013.

(51) Int. Cl.
*C07D 309/38* (2006.01)
(52) U.S. Cl.
CPC .................................. *C07D 309/38* (2013.01)
(58) Field of Classification Search
CPC ................................................... C07D 309/38
See application file for complete search history.

(56) References Cited

FOREIGN PATENT DOCUMENTS

| WO | WO2004/000792 A1 | * 12/2003 |
| WO | WO-2004000792 A1 | 12/2003 |
| WO | WO-2014189926 A1 | 11/2014 |

OTHER PUBLICATIONS

Wiley and Smith (Organic Syntheses, Coll. vol. 4, p. 201 (1963); vol. 31, p. 23 (1951)).*
"International Application Serial No. PCT/US2014/038784, International Search Report mailed Sep. 5, 2014", 4 pgs.
"International Application Serial No. PCT/US2014/038784, Written Opinion mailed Sep. 5, 2014", 4 pgs.
Campbell, et al., "Unsaturated lactones. Some esters of aconic and coumalic acids", J. Chem. Soc., (1947), 1176-1179.
Kaminski, T., et al., "Claisen Condensation of N-Methylpyrrolidinone and a-Chloronicotinic esters", J. Heterocyclic Chem., vol. 45, No. 1, (2008), 229-234.
Martinez, et al., "Mecanismo De La Reaccion De Compuestos 1, 3-Dicarboniucos Con Anhidrido Triflico. Ciclacion Anomala Del Ester Acetilacetico A 3-Etoxicarbonil-2, 6-Dimetil-4-Pirona", Anales De Quimica, vol. 91, No. 1.2, (1995), 121-123.
Rosenmund, P., et al., "Allo-, Epiallo- und Pseudoyohimbane sowie Heteroyohimbane durch Reaktion eines tetracyclischen Aldehyds mit Acetessigester in verschiedenen Lösungsmitteln", Liebigs Ann. Chem., No. 3, (1990), 233-238.
Von Pechmann, H., "Uber die Spaltungsprodukte der a-Oxysauren", Liebigs Ann. Chem., vol. 264, (1891), 261-309.

* cited by examiner

*Primary Examiner* — Valerie Rodriguez-Garcia
(74) *Attorney, Agent, or Firm* — Schwegman Lundberg & Woessner, P.A.

(57) ABSTRACT

A method to prepare coumalic acid comprising (a) heating a solution in dichloroethane of malic acid and sulfuric acid or a solution in dichloroethane of malic acid and a perfluorosulfonic acid or (b) adding an acid comprising sulfuric acid or a perfluorosulfonic acid to a solution of malic acid in dichloroethane to yield a solution that is heated for a period of time so as to convert the malic acid into a major amount of coumalic acid and, optionally, a minor amount of fumaric acid.

12 Claims, No Drawings

SYNTHESIS OF COUMALIC ACID

CROSS-REFERENCE TO RELATED APPLICATION

This application is a U.S. National Stage filing under 35 U.S.C. 371 from International Application No. PCT/US2014/038784, filed on May 20, 2014 and published as WO 2014/189926 on 27 Nov. 2014, which claims the benefit of priority to U.S. Provisional Patent Application Ser. No. 61/826,368, filed May 22, 2013, which applications and publications are incorporated herein in their entirety by reference.

STATEMENT OF GOVERNMENT RIGHTS

This invention was made with the support of the Department of Commerce under DOC Grant No. 057905210 and with the support of the National Science Foundation under NSF Grant No. EEC0813570. The U.S. Government has certain rights in this invention.

BACKGROUND OF THE INVENTION

The development of new, cost-competitive processes that utilize renewable resources as feedstocks is vital for a sustainable economy. These processes also represent important milestones toward the goal of reducing the United States' dependence on foreign oil. Introduction of such processes not only avoids the use of more petroleum, but also has the potential to provide substantial energy savings, and reduce greenhouse gas emissions. Although biobased synthesis of certain commercial significant compounds such as 1,3-propanediol have been reported,[1] there are comparatively few reported approaches to compounds related to terephthalic acid.[2]

Terephthalic acid (4-carboxybenzoic acid), is a commodity chemical produced from petroleum feedstocks. The most common synthesis pathway is the oxidation of para-xylene. Terephthalic acid and dimethyl terephthalate are employed in the preparation of polyethylene terephthalate (PET), a thermoplastic polymer used in many beverage and food containers and in fabrics, and polytrimethylene terephthalate, a material used in carpets and upholstery. Global production of terephthalic acid was near fifty million tons in 2009.

The regioselective Diels-Alder reactions of coumalic acid (1) with alpha-olefins has been reported,[3] as shown in Scheme 1, wherein R is alkyl, alkoxy, aryl, aryloxy, alkenyl and the like. The process involves a Diels-Alder reaction to produce a bicyclic intermediate that can be dehydrogenated by a Pd/C catalyst with loss of carbon dioxide to form the para-substituted benzoic acid in 99% para-selectivity and in yields in the range of 60-70%.

Scheme 1. Conversion of coumalic acid into para-substituted benzoic acids:

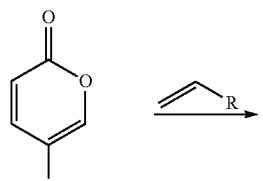

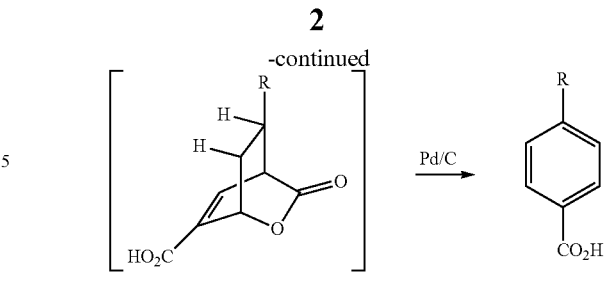

Dimethyl terephthalate can be prepared from methyl coumalate (1) by replacing R—CH=CH$_2$ with a captodative diene such as methyl (α-methoxy) acrylate.[4]

In order for the use of the Diels-Alder reaction to prepare terephthalic acid to become industrially useful, a viable and scalable synthesis of coumalic acid is needed. The conversion of malic acid (2) into coumalic acid is well known on a laboratory scale using concentrated sulfuric acid (97-98%) as the solvent and fuming sulfuric acid, a corrosive dehydrating agent, as the reagent. The reaction is conducted at 70° C. This transformation, shown in Scheme 2, was reported by von Pechmann in 1891 and appears to be the only reported preparation.[5] An *Organic Synthesis* article describes coumalic acid synthesis on a 100 gram scale using the von Pechmann conditions.[6]

Scheme 2. von Pechmann coumalic acid synthesis from malic acid (2):

Recently, Kaminski and Kirsh described a synthesis of 1 using a more concentrated solution of sulfuric acid.[7]

The intermediate in this transformation is formyl acetic acid (HO$_2$C—CH$_2$—CHO). Two molecules of this aldehyde acid react to produce one molecule of coumalic acid. Although this reaction is suitable for a multigram laboratory scale, scaling these corrosive reaction conditions to a pilot plant scale is not feasible.

The mechanism by which malic acid is transformed into the aldehyde acid was recently studied.[8] There is vigorous gas evolution at the beginning of the reaction. The gas is carbon monoxide, suggesting a direct protonation of the carboxylic acid as an early step. Interestingly, less than five percent of fumaric acid (3) is produced under these acidic conditions.

However, a need clearly exists for methods to produce coumalic acid (1) under milder conditions.

SUMMARY OF THE INVENTION

The present invention provides a method to prepare coumalic acid comprising heating a solution in dichloroethane of malic acid and sulfuric acid or a solution in dichloroethane of malic acid and a perfluorosulfonic acid, such as a perfluoro-alkyl sulfonic acid, e.g., perfluoro(C$_1$-C$_4$)alkyl sulfonic acid, so as to convert the malic acid into a major amount of coumalic acid and, optionally, a minor amount of fumaric acid.

One embodiment of the invention comprises adding an acid comprising sulfuric acid or a perfluorosulfonic acid to a solution of malic acid in dichloroethane to yield a solution that is heated for a period of time so as to convert the malic acid into coumalic acid, optionally, a minor amount of fumaric acid.

A further embodiment of the invention comprises adding an acid comprising sulfuric acid or triflic acid to a solution of ($C_1$-$C_4$)alkyl formyl acetate (methyl 3-oxo-propanoate) to yield a solution that is heated for a period of time so as to convert the methyl 3-oxo-propanoate directly to ($C_1$-$C_4$) alkyl coumalate, e.g., methyl coumalate.

Preferably the sulfuric acid or the perfluorosulfonic acid is present in an about 4-6 molar excess over the malic acid or the alkyl formyl acetate.

A further embodiment of the invention provides a method to prepare coumalic acid comprising heating a solution of malic acid in a mixture of sulfuric acid and trifluoroacetic acid so as to convert the malic acid into coumalic acid and, optionally, a minor amount of fumaric acid.

In this embodiment, the sulfuric acid and the trifluoroacetic acid are present in a molar ratio of about 1:1.

The present method provides a high yield of coumalic acid of about 40-95%, preferably about 51-86% yield, while limiting the amount of the side product, fumaric acid to about 1-5%.

Optionally, no fumaric acid is formed and/or the yield of coumalic acid is about 95-100%, based on the amount of the malic acid staring material.

The sulfuric acid that is employed in either case is concentrated sulfuric acid (97-98%), permitting the avoidance of fuming sulfuric acid and sulfur trioxide.

Preferably, the solutions are heated at about 75-110° C., such as at about 80-100° C., for a period of about 10-24 hrs, such as for about 15-20 hours.

The coumalic acid can be recovered and, optionally, esterified with a ($C_1$-$C_4$)alkanol, such as methanol, to yield a ($C_1$-$C_4$)alkyl coumalate, such as methyl coumalate. Both the free acid and the esters of coumalic acid can be subsequently converted to terephthalic acid or to a terephthalate diester, such as dimethyl terephthalate.

DETAILED DESCRIPTION OF THE INVENTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range, as would be recognized by one of ordinary skill in this art.

All percent compositions are given as weight-percentages, unless otherwise stated.

As used herein, the term "a major amount" is relative and indicates a yield of at least about 40-50% and "a minor amount" indicates a yield of less than about 10%.

When a group, e.g., an "alkyl" or a "perfluoroalkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl," "perfluoroalkyl" or other chemical group or moiety is definite and bounded, as the number of atoms in the group cannot be infinite.

Phrases such as "under conditions so as to provide," "to yield," "so as to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

Alkyl groups include straight chain and branched alkyl groups and cycloalkyl groups having from 1 to about 20 carbon atoms, and typically from 1 to 12 carbons or, in some embodiments, from 1 to 8 or 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups.

As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, halo, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups or arylalkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

From one to all of the hydrogen atoms on these groups may be replaced by fluorine to yield fluorinated alkyl, aryl, arylalkyl, cycloalkyl, (cycloalkyl)alkyl and the like. Perfluoroalkyl groups are preferred, e.g., as exemplified by perfluorobutylsulfonic acid or trifluoromethyl sulfonic acid.

The invention will be further described by reference to the following detailed Examples, wherein starting materials were commercially available. Product ratios were determined by $^1$H NMR integration (300 MHz) of crude mixtures of reaction products. $^1$H NMR data was consistent with literature reported values for coumalic acid, and fumaric acid (Aldrich Spectra Library).

EXAMPLE I

Coumalic Acid

Since a strong acid and heat will be needed to protonate the carboxylic acid, the effect of several strong anhydrous acids on malic acid was investigated. The results are summarized in Table 1. Solvent quantities of concentrated sulfuric acid afforded coumalic acid in good yield. Attempts to add a weaker co-acid lowered the reaction yields, with acetic acid not being successful and trifluoroacetic acid reducing the formation of 1 in Procedure B.

The respective anhydrides were also employed to consume water formed in the reaction, but there was no significant difference observed. Using acetic acid or trifluoroacetic acid without sulfuric acid present gave small amounts of o-acylated products and returned starting material.

The more strongly acidic sulfonic acids (triflic acid and nonafluorobutanesulfonic acid) gave coumalic acid in good yields, while methanesulfonic acid gave mixtures of 1 and 3 (Procedure C). Unexpectedly, para-toluenesulfonic acid (PTSA) gave a 71% yield of fumaric acid.

TABLE 1

Conversion of malic acid into coumalic acid.

| Acid | Temperature °C. | Solvent | Additive | Yield 1$^a$ | Yield 3$^a$ | Procedure |
|---|---|---|---|---|---|---|
| H$_2$SO$_4$ | 100 | Dichloroethane | None | 80$^b$ | 5 | A |
| H$_2$SO$_4$ | 120 | AcOH | None | 4 | 3 | B |
| H$_2$SO$_4$ | 120 | AcOH | Ac$_2$O | 6 | 9 | B |
| H$_2$SO$_4$ | 80 | CF$_3$CO$_2$H | None | 51 | 1 | B |
| H$_2$SO$_4$ | 80 | CF$_3$CO$_2$H | TFAA | 44 | 0 | B |
| MeSO$_3$H | 100 | Dichloroethane | None | 14 | 25 | C |
| CF$_3$SO$_3$H | 100 | Dichloroethane | None | 86$^b$ | 4 | C |
| C$_4$F$_9$SO$_3$H | 100 | Dichloroethane | None | 65 | 2 | C |
| PTSA | 120 | None | None | 0 | 71 | D |

$^a$based on $^1$H NMR integration
$^b$5 g scale

It should be noted that the amount of sulfuric acid used was reduced from 0.2 M when it was used as the solvent to 5 equivalents when dichloroethane was used as the solvent (Procedure A). The sulfonic acids were also used in lesser amounts (5 equivalents) to afford coumalic acid. When the reaction was scaled up with trifluoroacetic acid an 86% yield of coumalic acid was observed.

1) Procedure A:

To a solution of DL-malic acid (5 g, 37.29 mmol) in dichloroethane (75 mL) was added concentrated sulfuric acid (97-98%) (9.94 mL, 186.45 mmol) and the reaction mixture heated to 100° C. for 16 h. After cooling to 25° C. ("RT"), the red solution was poured onto ice and stirred for 30 mins. The mixture was extracted with EtOAc (3×) and the combined organic extracts were washed with ice-cold water (3×), dried over MgSO$_4$, and concentrated in vacuo to give a 16:1 mixture of coumalic acid (80% yield) and fumaric acid (5%).

2) Procedure B:

To a solution of DL-malic acid (0.268 g, 2 mmol) in concentrated H$_2$SO$_4$ (10 mL, 0.2 M) was added acetic acid or trifluoroacetic acid (10 mL, 0.2 M) and optionally acetic or trifluoroacetic anhydride (TFAA) (10 vol %) as noted on Table 1. The solution was heated to the temperature given on Table 1 for 16 h, cooled to RT and poured onto ice (50 g). After stirring for 30 min, the solution was extracted with EtOAc (25 mL×3). The combined organic extracts were washed with ice-cold water (25 mL×3), dried over MgSO$_4$, filtered and concentrated in vacuo to give the crude products, as indicated on Table 1.

3) Procedure C:

To a solution of DL-malic acid (0.268 g, 2 mmol) in dichloroethane (10 mL) was added sulfonic acid indicated on Table 1 (5 equiv) and the solution was heated to 100° C. for 16 h. After cooling to RT, the solution was poured onto ice (50 g) and stirred 30 min. The mixture was extracted with EtOAc (25 mL×3) and the combined organic extracts were washed with ice-cold water (25 mL×3), dried over MgSO$_4$, filtered and concentrated in vacuo to give the crude products.

4) Procedure D:

A mixture of L-malic acid and para-toluenesulfonic acid (PTSA) was heated to 120° C. with stirring, which resulted in melting of both solids into a red, viscous solution. After 16 h, the mixture was cooled to RT and quenched with H$_2$O, extracted with EtOAc and washed with brine. The combined organic layers were dried over MgSO$_4$, filtered and concentrated to give 3 as a tan solid in 71% yield.

EXAMPLE II

Methyl Coumalate

To a solution of methyl 3-oxo-propanoate (1.684 mmol) in dichloroethane (10 mL) was added concentrated sulfuric acid (5 equiv., 0.224 mL) or triflic acid (5 equiv., 0.373 mL) as shown on Scheme 3, below. The solution was heated to 100° C. for 16 h. After cooling to RT, the dark solution was quenched with a saturated solution of sodium bicarbonate and extracted with EtOAc (3×). The combined organic extracts were washed with brine, dried over MgSO$_4$, filtered and concentrated in vacuo to give the crude product which was purified by flash column chromatography (10:1-3:1 hexanes/ethyl acetate) to give methyl coumalate (62 mg, 48% yield using sulfuric acid; 83% yield using triflic acid).

Scheme 3:

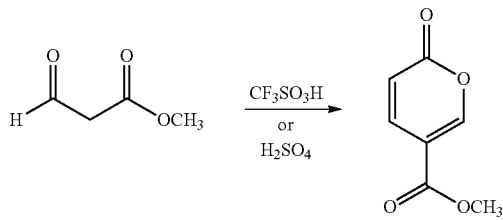

The following documents listed below, are incorporated by reference herein.

1. G. A. Kraus "Synthetic Methods for the Preparation of 1,3-Propanediol" *Clean Soil, Air, Water,* 36, 648 (2008).
2. Gong, W. H. (BP Corporation North America Inc., USA). Production of terephthalic acid from 2,5-furandicarboxylate. PCT Int. Appl. WO2009/064515 A1; Y. Matsushita et al., *Synth. Commun.,* 24, 3307 (1994).
3. Kraus, G. A.; Riley, S., Cordes, T. *Green Chemistry,* 2734-2736 (2011).
4. Kraus, G. A. et al., U.S. application Ser. No. 13/840,768, filed Mar. 15, 2013.
5. von Pechmann, *Ann.,* 264, 272 (1891).
6. Wiley, R. H.; Smith, N. R. *Organic Syntheses,* 4, 201 (1963).
7. Kaminski, T.; Kirsch, G. *J. Heterocyclic Chem.,* 45, 229 (2008).
8. Ashworth, I. W.; Bowden, M. C. et al. *Org. Process Res. Dev.,* 7, 74 (2003).

What is claimed is:

1. A method to prepare coumalic acid comprising heating a solution in dichloroethane of malic acid and sulfuric acid or a solution in dichloroethane of malic acid and a perfluorosulfonic acid so as to convert the malic acid into a major amount of coumalic acid and, optionally, a minor amount of fumaric acid.

2. A method to prepare coumalic acid comprising adding an acid comprising sulfuric acid or a perfluorosulfonic acid to a solution of malic acid in dichloroethane to yield a solution that is heated for a period of time so as to convert the malic acid into coumalic acid and, optionally, a minor amount of fumaric acid.

3. The method of claim 1 wherein the yield of coumalic acid is about 51-90%.

4. The method of claim 3 wherein the yield of fumaric acid is about 1-5%.

5. The method of claim 3 wherein no fumaric acid is formed.

6. The method of claim 1 wherein the sulfuric acid is concentrated sulfuric acid (97-98%).

7. The method of claim 1 wherein the sulfuric acid or the perfluoro sulfonic acid is present in an about 4-6 molar excess over the malic acid.

8. The method of claim 1 wherein the perfluorosulfonic acid is a perfluoroalkyl sulfonic acid.

9. The method of claim 1 wherein the solution that is heated is heated at about 75-110° C.

10. The method of claim 9 wherein the solution that is heated is heated for about 10-24 hrs.

11. A method to prepare (C$_1$-C$_4$)alkyl coumalate comprising heating a solution in dichloroethane of malic acid and sulfuric acid or a solution in dichloroethane of malic acid and a perfluorosulfonic acid so as to convert the malic acid into a major amount of coumalic acid and, optionally, a minor amount of fumaric acid;
further comprising reacting the coumalic acid with a (C$_1$-C$_4$)alkanol to yield (C$_1$-C$_4$)alkyl coumalate.

12. The method of claim 11 wherein the (C$_1$-C$_4$)alkanol is methanol.

* * * * *